United States Patent
Cooke et al.

(10) Patent No.: US 9,176,088 B2
(45) Date of Patent: Nov. 3, 2015

(54) METHOD AND APPARATUS FOR DETECTING SMOKE IN AN ION CHAMBER

(71) Applicant: Microchip Technology Incorporated, Chandler, AZ (US)

(72) Inventors: Benjamin T. Cooke, Denver, CO (US); Joseph Julicher, Maricopa, AZ (US); Keith Edwin Curtis, Gilbert, AZ (US)

(73) Assignee: MICROCHIP TECHNOLOGY INCORPORATED, Chandler, AZ (US)

( * ) Notice: Subject to any disclaimer, the term of this patent is extended or adjusted under 35 U.S.C. 154(b) by 413 days.

(21) Appl. No.: 13/667,196

(22) Filed: Nov. 2, 2012

(65) Prior Publication Data

US 2013/0154657 A1    Jun. 20, 2013

Related U.S. Application Data

(63) Continuation-in-part of application No. 13/633,686, filed on Oct. 2, 2012.

(60) Provisional application No. 61/570,485, filed on Dec. 14, 2011.

(51) Int. Cl.
| | |
|---|---|
| G01N 27/70 | (2006.01) |
| G01N 27/66 | (2006.01) |
| G08B 17/10 | (2006.01) |
| G08B 17/11 | (2006.01) |
| G01N 27/22 | (2006.01) |
| G01R 27/26 | (2006.01) |

(52) U.S. Cl.
CPC .............. *G01N 27/221* (2013.01); *G01N 27/66* (2013.01); *G01R 27/2605* (2013.01); *G08B 17/11* (2013.01)

(58) Field of Classification Search
USPC ........................................................ 324/469
See application file for complete search history.

(56) References Cited

U.S. PATENT DOCUMENTS

| | | | | |
|---|---|---|---|---|
| 3,295,121 | A | * 12/1966 | Meyer | 340/629 |
| 3,832,678 | A | 8/1974 | Gysell et al. | 340/587 |
| 4,213,047 | A | * 7/1980 | McCord | 250/381 |

(Continued)

FOREIGN PATENT DOCUMENTS

| | | | | |
|---|---|---|---|---|
| DE | 102009030495 A1 | 1/2011 | | G01B 7/00 |
| EP | 1719947 A1 | 11/2006 | | F23N 5/12 |

(Continued)

OTHER PUBLICATIONS

International Search Report and Written Opinion, Application No. PCT/US2013/052956, 12 pages, Jan. 28, 2014.

(Continued)

*Primary Examiner* — Melissa Koval
*Assistant Examiner* — Courtney McDonnough
(74) *Attorney, Agent, or Firm* — Slayden Grubert Beard PLLC

(57) ABSTRACT

A smoke detection sensor ion chamber has a capacitance and a change in the permittivity of that capacitance dielectric (ionized air in the chamber) may be used to detect the presence of smoke therein. Smoke from typical fires is mainly composed of unburned carbon that has diffused in the surrounding air and rises with the heat of the fire. The permittivity of the carbon particles is about 10 to 15 times the permittivity of clean air. The addition of the carbon particles into the air in the ion chamber changes in the permittivity thereof that is large enough to measure by measuring a change in capacitance of the ion chamber.

23 Claims, 6 Drawing Sheets

(56) References Cited

U.S. PATENT DOCUMENTS

| | | | |
|---|---|---|---|
| 4,222,045 A | 9/1980 | Cholin | 340/628 |
| 4,260,984 A | 4/1981 | Honma | 340/630 |
| 4,266,220 A * | 5/1981 | Malinowski | 340/630 |
| 4,401,978 A | 8/1983 | Solomon | 340/628 |
| 4,538,137 A | 8/1985 | Kimura | 340/512 |
| 4,652,866 A | 3/1987 | Siegmann et al. | 340/628 |
| 5,173,683 A | 12/1992 | Brighenti et al. | 340/505 |
| 5,243,330 A | 9/1993 | Thuillard | 340/629 |
| 5,422,807 A | 6/1995 | Mitra et al. | 700/79 |
| 5,633,591 A | 5/1997 | Childress et al. | 324/399 |
| 5,705,988 A | 1/1998 | Mcmaster | 340/628 |
| 5,966,078 A * | 10/1999 | Tanguay | 340/636.1 |
| 6,257,049 B1 * | 7/2001 | Greybush | 73/29.01 |
| 6,433,712 B1 | 8/2002 | Ohnhaeuser et al. | 341/118 |
| 6,661,346 B1 | 12/2003 | Wood et al. | 340/601 |
| 6,981,090 B1 | 12/2005 | Kutz et al. | 710/317 |
| 7,288,946 B2 | 10/2007 | Hargreaves et al. | 324/678 |
| 7,307,485 B1 | 12/2007 | Snyder et al. | 331/150 |
| 7,382,140 B2 | 6/2008 | Obrecht | 324/678 |
| 7,460,441 B2 | 12/2008 | Bartling | 368/118 |
| 7,764,213 B2 | 7/2010 | Bartling et al. | 341/152 |
| 8,031,094 B2 | 10/2011 | Hotelling et al. | 341/143 |
| 8,487,655 B1 | 7/2013 | Kutz et al. | 326/86 |
| 8,547,135 B1 | 10/2013 | Yarlagadda et al. | 326/38 |
| 8,847,802 B2 | 9/2014 | Lundstrum et al. | 341/141 |
| 8,884,771 B2 | 11/2014 | Cooke et al. | 340/628 |
| 8,981,754 B1 | 3/2015 | Rohilla et al. | 323/312 |
| 2002/0078744 A1 | 6/2002 | Gehman et al. | 73/204.11 |
| 2002/0101345 A1 | 8/2002 | Pattok et al. | 340/516 |
| 2002/0153923 A1 | 10/2002 | Piasecki et al. | 326/57 |
| 2003/0058114 A1 | 3/2003 | Miller | 340/577 |
| 2004/0257235 A1 | 12/2004 | Right et al. | 340/628 |
| 2005/0030172 A1* | 2/2005 | Right et al. | 340/521 |
| 2007/0075710 A1 | 4/2007 | Hargreaves et al. | 324/658 |
| 2008/0012715 A1 | 1/2008 | Montgomery | 340/579 |
| 2008/0079148 A1 | 4/2008 | Leung et al. | 257/734 |
| 2008/0111714 A1 | 5/2008 | Kremin | 341/33 |
| 2008/0272826 A1 | 11/2008 | Smit et al. | 327/509 |
| 2008/0312857 A1 | 12/2008 | Sequine | 702/65 |
| 2009/0230305 A1* | 9/2009 | Burke et al. | 250/336.1 |
| 2009/0256817 A1 | 10/2009 | Perlin et al. | 345/174 |
| 2010/0059295 A1 | 3/2010 | Hotelling et al. | 178/18.06 |
| 2010/0060593 A1 | 3/2010 | Krah | 345/173 |
| 2010/0097015 A1 | 4/2010 | Knoedgen et al. | 318/135 |
| 2010/0102832 A1 | 4/2010 | Bartling et al. | 324/679 |
| 2010/0181180 A1 | 7/2010 | Peter | 200/5 R |
| 2010/0231241 A1 | 9/2010 | Mueck et al. | 324/686 |
| 2010/0283760 A1 | 11/2010 | Leung et al. | 345/174 |
| 2010/0287571 A1 | 11/2010 | Mohammed et al. | 719/328 |
| 2010/0295555 A1* | 11/2010 | Emanuel et al. | 324/601 |
| 2011/0007028 A1 | 1/2011 | Curtis et al. | 345/174 |
| 2011/0234417 A1 | 9/2011 | Aleman et al. | 340/660 |
| 2011/0267287 A1 | 11/2011 | Bartling et al. | 345/173 |
| 2011/0267309 A1 | 11/2011 | Hanauer et al. | 345/174 |
| 2012/0005693 A1 | 1/2012 | Mohammed et al. | 719/328 |
| 2012/0098686 A1 | 4/2012 | Wang | 341/118 |
| 2012/0112728 A1 | 5/2012 | Bodo et al. | 323/311 |
| 2013/0088246 A1 | 4/2013 | Lundstrum et al. | 324/686 |
| 2013/0090873 A1 | 4/2013 | Lundstrum et al. | 702/64 |
| 2013/0126715 A1 | 5/2013 | Flaherty | 250/214 R |
| 2013/0298100 A1 | 11/2013 | Hastings et al. | 716/126 |
| 2013/0322439 A1 | 12/2013 | Verhollen et al. | 370/389 |

FOREIGN PATENT DOCUMENTS

| | | | | |
|---|---|---|---|---|
| FR | 2473201 A1 | | 7/1981 | G08B 17/11 |
| GB | 1598821 A | | 9/1981 | G08B 17/11 |
| GB | 2117560 A | * | 10/1983 | G01N 27/22 |
| GB | 2156126 A | | 10/1985 | G08B 17/00 |
| WO | 2006/138205 A1 | | 12/2006 | H03M 1/06 |

OTHER PUBLICATIONS

Yair, R., "Charge Sampling Method for Low Current Measurement," Review of Scientific Instruments, vol. 45, No. 3, 6 pages, Mar. 1974.

Margarita, Andrey, "Application Note AN2245: Smart Smoke Detector," Cypress Semiconductor Corporation, XP055054690, URL: http://www.psocdeveloper.com/uploads/tx_piapappnote/an2245_01.pdf, 12 pages, Feb. 22, 2005.

Perme, Thomas, "AN1101: Introduction to Capacitive Sensing," Microchip Technology, Inc., XP002693941, URL: http://ww1.microchip.com/downloads/en/AppNotes/01101A.pdf, 10 pages, Jun. 25, 2007.

Bohn, Bruce, "AN1250: Microchip CTMU for Capacitive Touch Applications," Microchip Technology, Inc., XP055007432, URL: http://www.microchip.com/stellent/ideplg?IdcService=SS_GET_PAGE&nodeID=1824&appnote=en539441, 22 pages, Feb. 3, 2009.

Perme, Thomas et al., AN1298: Capacitive Touch Using Only an ADC ("CVD"), Microchip Technology, Inc., XP055007357, URL: http://www.microchip.com/stellent/idcplg?IdcService=SS_GET_PAGE&nodeId=1824&appnote=en545264, 4 pages, Oct. 7, 2009.

Davison, Burke, "AN1334: Techniques for Robust Touch Sensing Design," Microchip Technology, Inc., XP055047201, URL: http://www.microchip.com/downloads/en/AppNotes/01334A.pdf, 28 pages, Aug. 6, 2010.

Yedamale, Padmaraja et al., "AN1375: See What You Can Do with the CTMU," Microchip Technology, Inc., XP055047211, URL: http://www.microchip.com/downloads/en/AppNotes/CTMU%2001375a.pdf, 12 pages, May 11, 2011.

Anonymous, "Delta-Sigma Modulation," Wikipedia, URL: http://en.wikipedia.org/w/index.php?title=Special:Book&bookcmd=download&collection_id=fa136df1282a073a&writer=rl&return_to=Delta-sigma modulation, 14 pages, 2012.

international Search Report and Written Opinion, Application No. PCT/US2012/058682, 12 pages, Dec. 17, 2012.

International Search Report and Written Opinion, Application No. PCT/US2012/058691, 13 pages, Dec. 19, 2012.

International Search Report and Written Opinion, Application No. PCT/US2012/058832, 11 pages, Jan. 22, 2013.

International Search Report and Written Opinion, Application No. PCT/US2012/058837, 14 pages, Feb. 18, 2013.

International Search Report and Written Opinion, Application No. PCT/US2012/058716, 10 pages, Mar. 15, 2013.

International Search Report and Written Opinion, Application No. PCT/US2012/069086, 10 pages, Apr. 5, 2013.

International Search Report and Written Opinion, Application No. PCT/US2012/069094, 12 pages, Apr. 5, 2013.

International Search Report and Written Opinion, Application No. PCT/US2012/058688, 11 pages, Apr. 5, 2013.

International Search Report and Written Opinion, Application No. PCT/US2012/069076, 11 pages, Apr. 10, 2013.

International Search Report and Written Opinion, Application No. PCT/US2012/070466, 13 pages, Apr. 24, 2013.

U.S. Advisory Action, U.S. Appl. No. 13/709,399, 3 pages, Sep. 8, 2015.

* cited by examiner

METHOD AND APPARATUS FOR DETECTING SMOKE IN AN ION CHAMBER

RELATED PATENT APPLICATION

This application claims priority to commonly owned U.S. Provisional Patent Application Ser. No. 61/570,485; filed Dec. 14, 2011; entitled "Method and Apparatus for Detecting Smoke," by Benjamin T. Cooke, Joseph Julicher and Keith Edwin Curtis; and is a Continuation-In-Part of U.S. patent application Ser. No. 13/633,686; filed Oct. 2, 2012; entitled "Differential Current Measurements to Determine Ion Current in the Presence of Leakage Current," by Joseph Julicher, Keith Curtis and Paul N. Katz; both of which are hereby incorporated by reference herein for all purposes.

TECHNICAL FIELD

The present disclosure relates to smoke detection devices, and more particularly, to a smoke detection device that uses a change in permittivity that affects a capacitance value of an ion chamber when smoke is introduced therein.

BACKGROUND

A smoke detector generally uses an ionization chamber containing a radioactive ion source that is coupled to a high input impedance operational amplifier. FIG. 1 shows a typical ionization chamber used in a smoke detector to produce a very small current (nA) that is reduced in the presence of smoke particles. Operational amplifiers are used to convert this current to a voltage that is then measured to determine the presence of smoke. Elevated temperatures cause increased leakage currents on the inputs of the operational amplifier in the smoke detector. This affects overall performance of the ionization chamber smoke detection function. Thus, such increases in leakage currents can pose a variety of problems such as inaccuracy, etc. which may require further compensation circuits when designing a smoke detector and therefore may increase the cost of the device.

Furthermore, the impedance of the ion chamber is extremely high, and any leakage currents, e.g., printed circuit board leakage current, masks the ion chamber current. Smoke detection ion chambers therefore require a complex manufacturing process where pins of the sensing integrated circuit operational amplifier are bent and directly welded in mid-air to the ion chamber. As mentioned above, special low leakage circuits are required to detect the small current change through the ion chamber caused by the presence of smoke therein.

SUMMARY

Therefore, a need exists for a way to detect smoke in an ion chamber of a smoke detector that does not require sensitive and expensive components nor complex manufacturing processes.

According to an embodiment, a method for detecting smoke may comprise the steps of: coupling an ionization chamber to a capacitive voltage divider (CVD) circuit; determining a change in a capacitance of the ionization chamber using the CVD circuit; and detecting the presence of smoke by detecting a predetermined change in the capacitance.

According to a further embodiment of the method, the step of determining the change in the capacitance of the ionization chamber may further comprise the steps of: determining a first change in the capacitance of the ionization chamber when the ionization chamber may be at a first polarity; determining a second change in the capacitance of the ionization chamber when the ionization chamber may be at a second polarity; determining a difference between the first change and the second change; and using the difference in determining the change in the capacitance of the ionization chamber. According to a further embodiment of the method, the predetermined change in the capacitance may be a change in the capacitance within a certain time.

According to a further embodiment of the method, the step of determining the change in the capacitance of the ionization chamber may comprise the steps of: charging the capacitance of a first capacitor to a first voltage; charging the capacitance of the ionization chamber to a second voltage; coupling the first capacitor to the capacitance of the ionization chamber, wherein a third voltage on the first capacitor and the capacitance of the ionization chamber results; converting the third voltage to a digital representation thereof; comparing the digital representation of the converted third voltage with a previously stored digital representation thereof; detecting the presence of smoke when the digital representation of the converted third voltage has changed from the previously stored digital representation by at least the predetermined change; and storing the digital representation of the third voltage.

According to a further embodiment of the method, the step of determining the change in the capacitance of the ionization chamber may comprise the steps of: charging the capacitance of a first capacitor to a first voltage; charging the capacitance of a first ionization chamber open to smoke entrance to a second voltage; coupling the first capacitor to the capacitance of the first ionization chamber, wherein a third voltage on the first capacitor and the capacitance of the first ionization chamber results; converting the third voltage to a digital representation thereof; storing the digital representation of the third voltage; charging the capacitance of the first capacitor to a fourth voltage; charging the capacitance of a second ionization chamber closed to smoke entrance to a fifth voltage; coupling the first capacitor to the capacitance of the second ionization chamber, wherein a sixth voltage on the first capacitor and the capacitance of the second ionization chamber results; converting the sixth voltage to a digital representation thereof; storing the digital representation of the sixth voltage; subtracting the digital representation of the third voltage from the digital representation of the sixth voltage and dividing by the digital representation of the sixth voltage to produce a resulting representation; comparing the resulting representation with a previously stored resulting representation; detecting the presence of smoke when the resulting representation has changed from the previously stored resulting representation by at least the predetermined change; and storing the resulting representation; According to a further embodiment of the method, where: in a first measurement, a housing of the ionization chamber may be coupled to the CVD circuit; and in a second measurement, a collector plate of the ionization chamber may be coupled to the CVD circuit.

According to a further embodiment of the method, further steps may comprise the steps of subtracting a measurement value of the first measurement from a measurement value of the second measurement then dividing by the second measurement value; and comparing the count numbers of subsequent time periods to determine whether the count number of any one or more of the subsequent time periods has changed by a certain number of counts. According to a further embodiment of the method, a further step may comprise the step of compensating for temperature change with temperature information from a temperature sensor. According to a further embodiment of the method, a further step may comprise the step of compensating for relative humidity change with relative humidity information from a relative humidity sensor.

According to a further embodiment of the method, a further step may comprise the step of compensating for voltage change with voltage information from a voltage sensor. According to a further embodiment of the method, the first voltage may be approximately a power supply voltage and the second voltage may be approximately a power supply common. According to a further embodiment of the method, the first voltage may be approximately a power supply common and the second voltage may be approximately a power supply voltage. According to a further embodiment of the method, the fourth voltage may be approximately a power supply voltage and the fifth voltage may be approximately a power supply common. According to a further embodiment of the method, the fourth voltage may be approximately a power supply common and the fifth voltage may be approximately a power supply voltage.

According to another embodiment, an apparatus for detecting smoke may comprise: an ionization chamber coupled to a capacitive voltage divider (CVD) circuit for determining a capacitance of the ionization chamber; wherein a predetermined change in the capacitance of the ionization chamber indicates the presence of smoke in the ionization chamber.

According to a further embodiment, circuits may be provided for alternately coupling to the ionization chamber at a first polarity for determining a first capacitance of the ionization chamber and coupling to the ionization chamber at a second polarity for determining a second capacitance of the ionization chamber, whereby a difference between the first and second capacitances may be used in determining the presence of smoke in the ionization chamber. According to a further embodiment, the CVD circuit may be a peripheral device in a microcontroller. According to a further embodiment, a digital processor and memory may be coupled to the CVD circuit and an alarm circuit.

According to a further embodiment, a temperature sensor may be coupled to the digital processor and a temperature compensation look-up table stored in the memory coupled to the digital processor and used to compensate temperature induced changes of the capacitance of the ionization chamber. According to a further embodiment, a humidity sensor may be coupled to the digital processor and a humidity compensation look-up table stored in the memory coupled to the digital processor and used to compensate humidity induced changes of the capacitance of the ionization chamber. According to a further embodiment, a voltage sensor may be coupled to the digital processor and a voltage compensation look-up table stored in the memory coupled to the digital processor and used to compensate voltage induced changes of the capacitance of the ionization chamber. According to a further embodiment, an audible alert may be actuated by the presence of smoke in the ionization chamber. According to a further embodiment, a visual alert may be actuated by the presence of smoke in the ionization chamber.

According to yet another embodiment, an apparatus for detecting smoke may comprise: a first ionization chamber coupled to a capacitive voltage divider (CVD) circuit for determining a capacitance of the first ionization chamber, wherein the first ionization chamber may be open to smoke entrance; a second ionization chamber coupled to the CVD circuit for determining a capacitance of the second ionization chamber, wherein the second ionization chamber may be closed to smoke entrance; wherein a predetermined difference in the capacitances of the first and second ionization chambers indicates the presence of smoke in the first ionization chamber. According to a further embodiment, a smoke detection timer may be used in determining whether the predetermined difference occurs within a certain time period.

BRIEF DESCRIPTION OF THE DRAWINGS

A more complete understanding of the present disclosure may be acquired by referring to the following description taken in conjunction with the accompanying drawings wherein.

Figure 1:
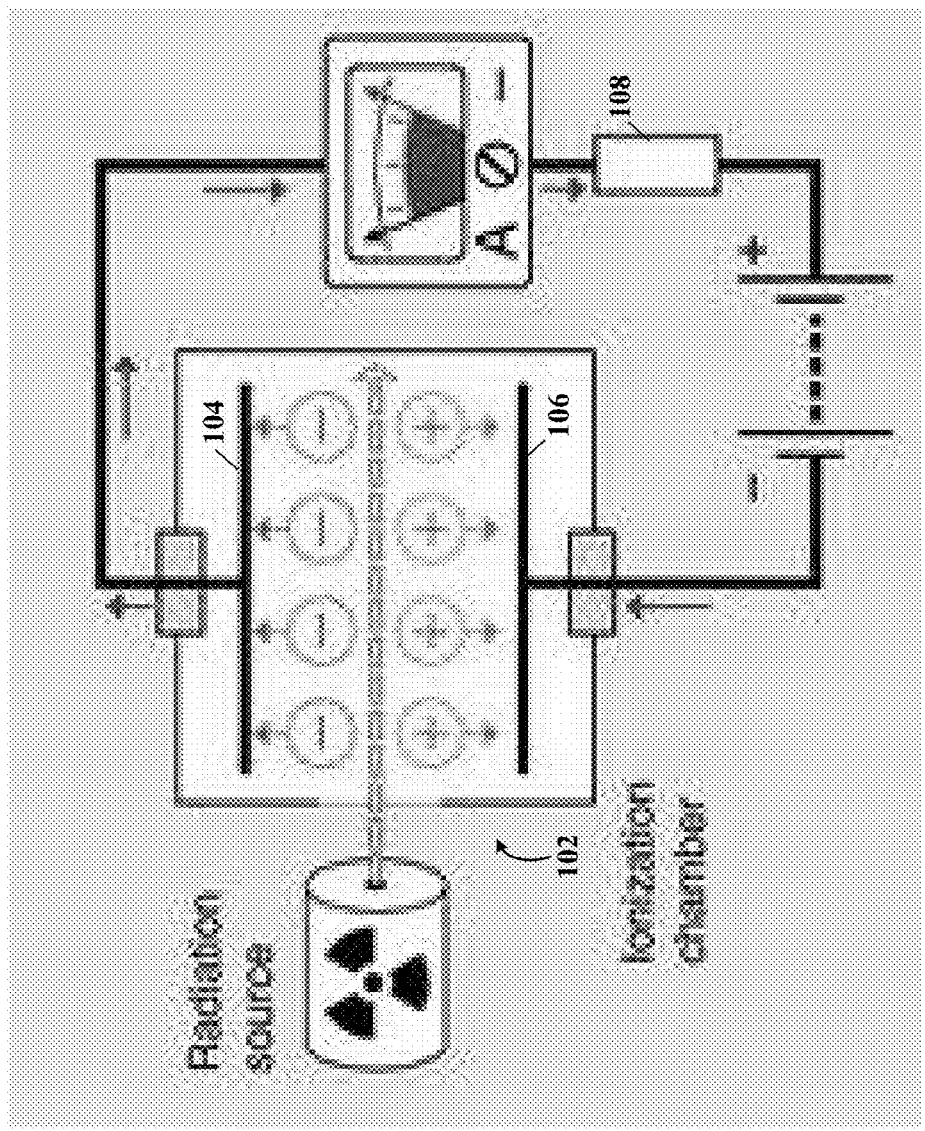
FIG. 1 illustrates a schematic diagram of an ion chamber having a radiation source and used as a smoke detection sensor.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION

A radioactive source in an ion chamber causes some of the gas (e.g., air) in the chamber to ionize. The results is a higher than normal permittivity of the gas due to the higher than normal number of electrically polarized (ionized) gas molecules. When smoke enters the ion chamber, the smoke reacts with the ionized gas molecules thereby changing the permittivity, $\in$, thereof. The ion chamber may be characterized as a leaky capacitor with the amount of leakage current determined by the ion flow between charged plates 102 and 104 (FIG. 1) of the ion chamber. A capacitance, C, of a capacitor formed by plates 102 and 104 is a function of the area, A, of the conductive plates 102 and 104; the distance, d, between the plates 102 and 104; and the permittivity, $\in$, of the dielectric (air) therebetween according to the formula: $C=\in A/d$. Thus a change in the permittivity of the gas in the ion chamber also changes the capacitance value thereof. Therefore, by using a capacitance measuring function, e.g., a capacitive voltage divider (CVD) in a microcontroller, the capacitance value change caused by the permittivity change of the gas dielectric of this leaky capacitor can be detected to determine the presence of smoke therein.

Microcontrollers now include peripherals that enhance the detection and evaluation of such capacitive value changes. One such application utilizes the capacitive voltage divider (CVD) method to determine a capacitance value and/or evaluate whether the capacitive value has changed. The CVD method is more fully described in Application Note AN1208, available at www.microchip.com; and a more detailed explanation of the CVD method is presented in commonly owned United States Patent Application Publication No. US 2010/0181180, entitled "Capacitive Touch Sensing using an Internal Capacitor of an Analog-To-Digital Converter (ADC) and a Voltage Reference," by Dieter Peter; wherein both are hereby incorporated by reference herein for all purposes. It is also contemplated and within the scope of this disclosure that any type of capacitance measurement circuit having the necessary resolution may be used in determining the capacitance value and/or change in the capacitance value of the ion chamber, and that a person having ordinary skill in the art of electronics and having the benefit of this disclosure could implement such a capacitance measurement circuit.

Temperature and battery voltage variations can make significant differences in the permittivity of the gas (air) with corresponding variations in the capacitance measurements of a first ion chamber. By providing a second ion chamber that is sealed from smoke entering, a comparison of the measured capacitance values of each of the first and second ion chambers can be used to compensate for these variations and provide a sensitive way of detecting smoke particles. For example, subtracting the first ion chamber capacitance value from the second ion chamber capacitance value and then dividing by the second ion chamber capacitance value, removes the temperature and battery voltage effects, leaving a resultant value with is primarily affected by the presence of smoke in the first ion chamber.

Temperature, relative humidity (RH) and/or battery voltage sensors may be incorporated into a smoke detection system for determining the compensation necessary for the capacitance measurements of the ion chamber used for smoke detection. Permittivity variations due to temperature, RH and/or voltage changes generally are over a longer time period than a sudden change in the amount of contaminates (carbon particles, etc.) in the air between the plates of the ion chamber capacitor. Another less sensitive way to ignore permittivity variations due to temperature, RH and/or voltage changes, would be to use an envelope detection or averaging process to ignore the slow drift of ion chamber capacitance due to voltage and/or temperature changes but recognize a more abrupt (rapid) change of the permittivity of air due to carbon particles suddenly showing up in the ion chamber. Various techniques for measuring changes in capacitance may be used and are contemplated herein for all purposes. Those having ordinary skill in capacitor measurement circuits and the benefit of this disclosure could readily apply those capacitor measurement circuits in a smoke detection apparatus. A mixed signal (analog and digital functions) microcontroller may used for capacitance measurements, e.g., CVD, using an analog-to-digital converter (ADC) in the microcontroller, doing the calculations necessary to determine whether smoke is present in the ion chamber, and compensate for and/or average out permittivity changes due to temperature, RH and/or battery voltage changes.

Referring now to the drawing, the details of specific example embodiments are schematically illustrated. Like elements in the drawings will be represented by like numbers, and similar elements will be represented by like numbers with a different lower case letter suffix.

Referring to FIG. 1, depicted is a schematic diagram of an ion chamber having a radiation source and used as a smoke detection sensor. The ion chamber 102 may be characterized as a capacitor with some ionized gas molecules between the capacitor plates 104 and 106. The gas molecules are ionized by the radiation source and when a voltage is applied between the two capacitor plates 104 and 106 a current will flow through the ionized gas and a resistor 108 connected in series with the capacitor plates 104 and 106. This current produces a voltage across the resistor 108. By measuring the voltage across the resistor 108, the permittivity, $\in$, of the gas may be determined. Smoke in the ion chamber will cause an abrupt change in the permittivity, $\in$, causing an abrupt change in the current flow and voltage across the resistor 108. This voltage is measured by a very high impedance operational amplifier (not shown) which requires complex circuitry and manufacturing processes. A better way, according to the teachings of this disclosure, is to measure the capacitance values of the ion chamber before and after smoke entry therein. As the ionized gas permittivity, $\in$, changes so does the capacitance value of the ion chamber. By using a capacitive measurement module having high enough capacitance value measurement resolution, the change in capacitance caused by smoke entry into the ion chamber may be detected and used to generate a smoke detection alarm.

Figure 1A:
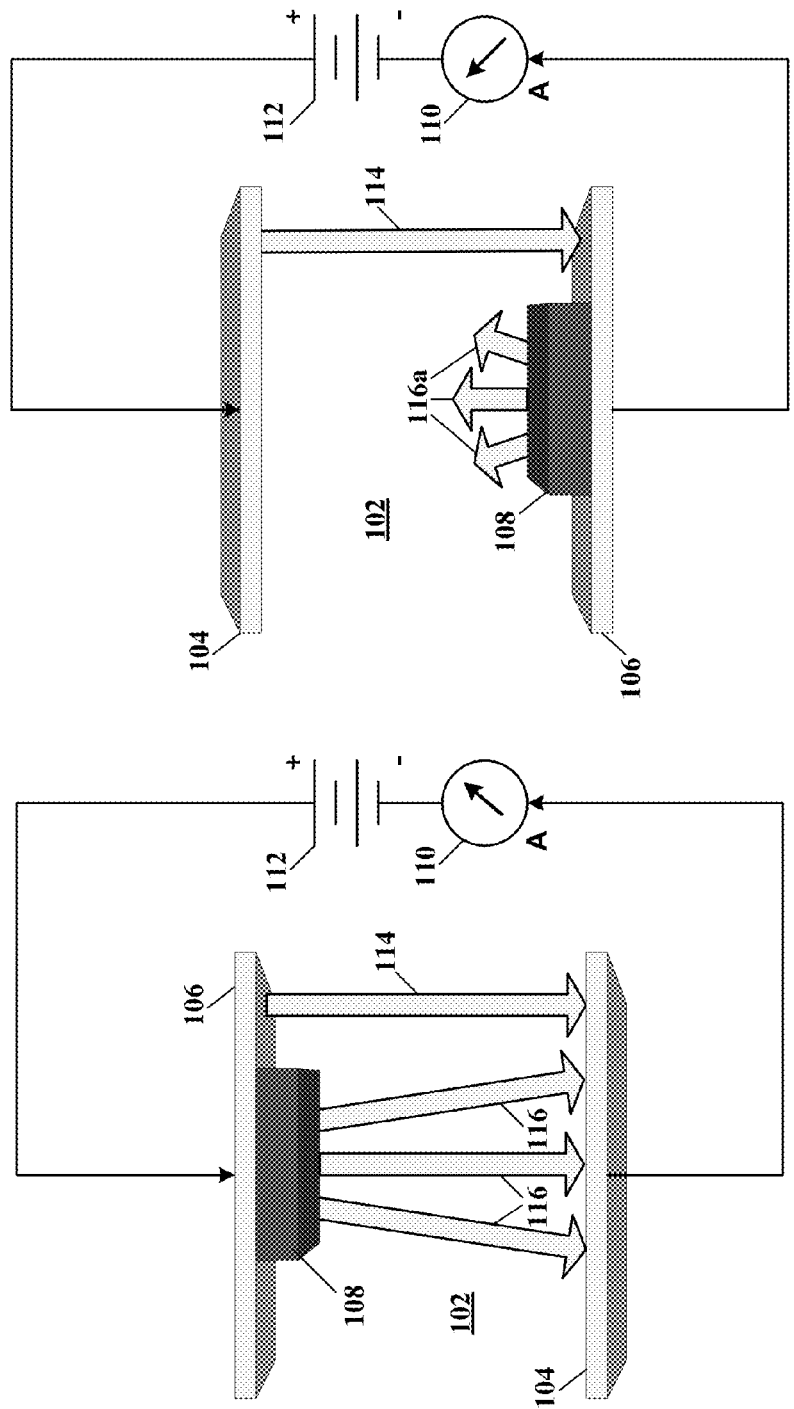
FIG. 1A illustrates schematic diagrams of an ion chamber having a radiation source and showing current flows therethrough for different polarity voltage source connections thereto.

Referring to FIG. 1A, depicted are schematic diagrams of an ion chamber having a radiation source and showing current flows therethrough for different polarity voltage source connections thereto. The ion chamber 102 may be characterized as three electrodes, e.g., electrodes 104, 106 and 210, having some ionized gas (e.g., air) molecules therebetween. The gas molecules are ionized by a radiation source 108. When a voltage potential 112 is applied between the two electrodes 104 and 106 at a first polarity (positive to electrode 106 and negative to electrode 104), a positively biased ionization electron current 116, $I_{chamber}$, will flow through the ionized gas. When the voltage potential 112 is applied between the two electrodes 104 and 106 at a second polarity (positive to electrode 104 and negative to electrode 106), substantially no negatively biased ionization electron current 116a will flow through the ionized gas since now the electrode 104 will repel the ionized gas electrons. However, leakage current 114, $I_{leakage}$, e.g., printed circuit board contaminates, grease, dust, etc., will flow irrespective of the connected polarity of the voltage potential 112.

Thus when the voltage potential 112 is connected at the first polarity across chamber 102 electrodes 104 and 106, the total current flow through the current meter 110 is the ionized electron current 116, $I_{chamber}$, plus the leakage current 114, $I_{leakage}$. And when the voltage potential 112 is connected at the second polarity across chamber 102 electrodes 104 and 106, the total current flow through the current meter 110 is substantially no ionized electron current 116a plus the leakage current 114, $I_{leakage}$, which results in substantially only the leakage current 114, $I_{leakage}$. Therefore, by subtracting the leakage current 114, $I_{leakage}$, from the total current flow, the actual ionized electron current 116, $I_{chamber}$, may be determined. This allows more sensitive measurements of any change in the ionized electron current 116, $I_{chamber}$, without these changes being masked by the undesired leakage current 114, $I_{leakage}$. It is contemplated and within the scope of this disclosure that any fluid, e.g., gas or liquid, that can be ionized by the ion source 108 will function as described hereinabove.

Figure 2:
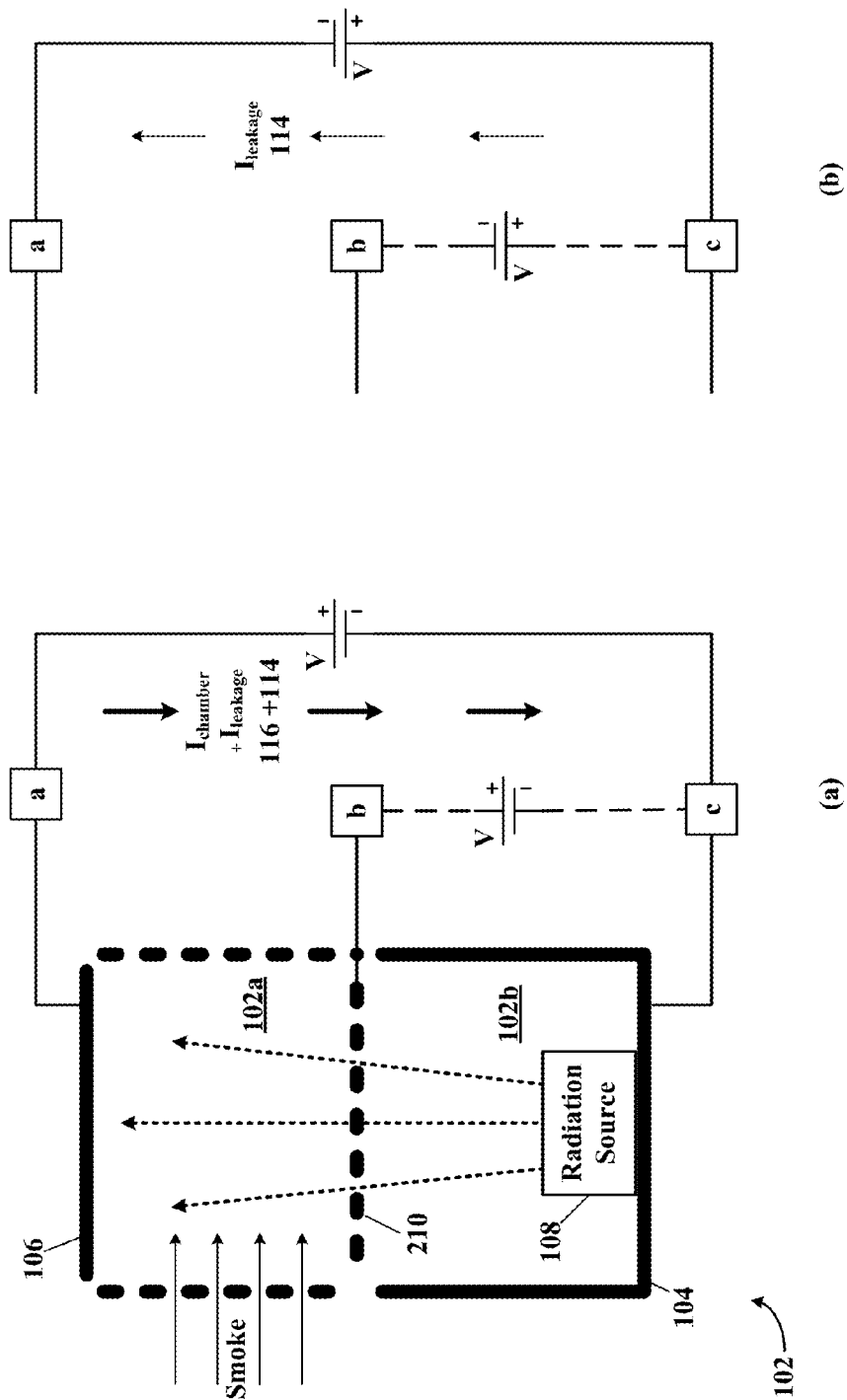
FIG. 2 illustrates a schematic elevational view of a typical ion chamber used as a smoke detection sensor.

Referring to FIG. 2, depicted is a schematic elevational view of a typical two chamber smoke detection sensor having a radiation source. The ion chamber 102 is comprised of two chambers 102a and 102b. The top chamber 102a is open to ingress of smoke therein, and the bottom chamber 102b is closed to smoke ingress. A conductive screen 210 is located between the two chambers 102a and 102b. The radiation source 108 proximate to or in the ion chamber 102 causes some of the gas in the chambers 102a and 102b to ionize. This ionization of the gas within the chambers 102a and 102b causes an ionization current 116, $I_{chamber}$, through both chambers 102a and 102b to increase between the electrodes 104 and 106 of the ion chamber 102.

When smoke is present in the top chamber 102a, it combines with the ionized gas, neutralizing some of the ionized gas from the current path of the ionization current 116, $I_{chamber}$. As a result the permittivity of the top chamber 102a is smaller than it is in the lower chamber 102b. The ionization current 116, $I_{chamber}$, flows in series through chambers 102a and 102b and therefore will be lower when smoke is in the chamber 102a. When the voltage across the chambers 102a and 102b is reversed substantially no reverse ionization current 116a will flow and the only current flow between the electrodes 104 and 106 will be the leakage current 114. The presence of the leakage current 114 reduces the sensitivity in measuring changes in the ionization current 116. By removing this common mode leakage current 114 from the determination of smoke in the chamber 102a, a more sensitive smoke detector results.

Figure 3:
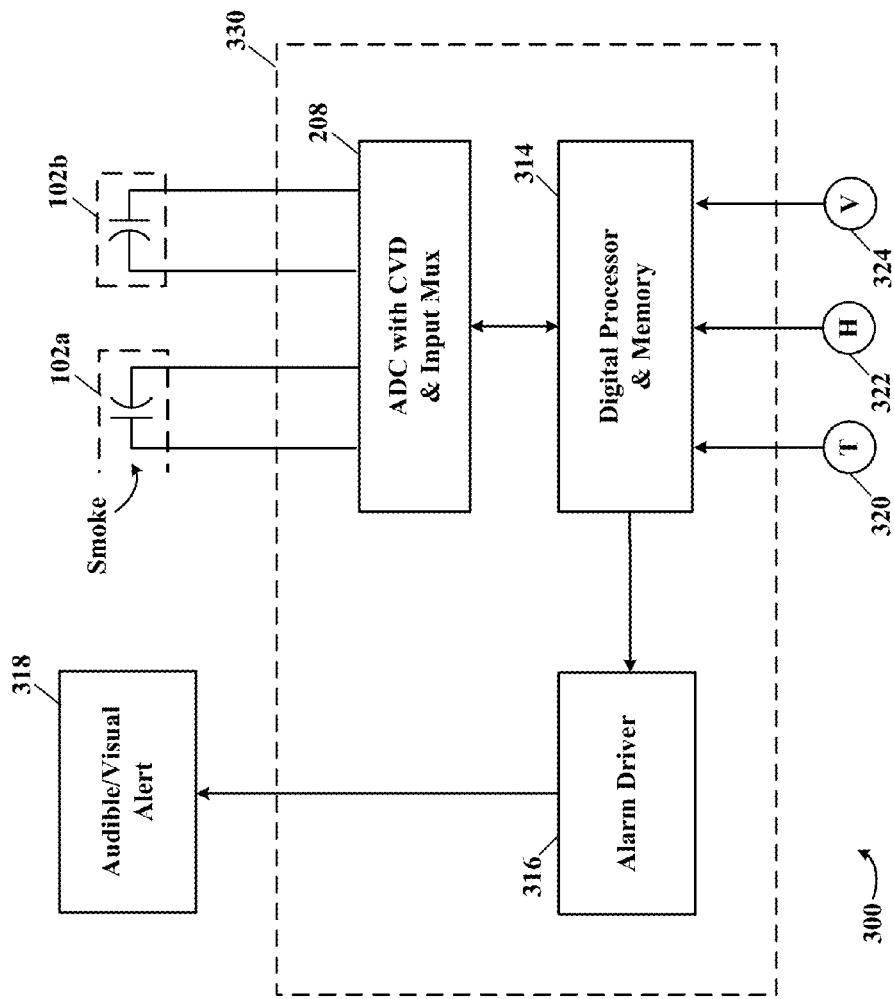
FIG. 3 illustrates a schematic block diagram of a smoke detector, according to a specific example embodiment of this disclosure.

Referring to FIG. 3, depicted is a schematic block diagram of a smoke detector, according to a specific example embodiment of this disclosure. A smoke detector, generally represented by the numeral 300, may comprise an analog-to-digital converter (ADC) 208 having capacitive voltage divider (CVD) and input multiplexing functions, a smoke detection sensor ion chamber 102a, a digital processor and memory 314, an alarm driver 316, and an audible/visual alert 318. The ADC 208, digital processor and memory 314, and alarm driver 316 may be provided in an integrated circuit microcontroller 330. The smoke detection sensor ion chamber 102a is coupled to the ADC 208 wherein representations of capacitance values thereof are measured and then each representative capacitance value is read by and processed in the digital processor and memory 314. When there is a change in the capacitance value representations within a certain time, the digital processor 314 will enable the alarm driver 316 which turns on the audible/visual alert 318 to indicate the presence of smoke in the location of the smoke detector 300.

The smoke detector 300 may further comprise a second ion chamber 102b that is closed to outside air that may contain smoke. The first and second ion chambers 102a and 102b may be used for making a comparison of the measured capacitance values of each of the first and second ion chambers 102a and 102b, and compensate for these variations, thereby providing for a more sensitive way of detecting smoke particles, as more fully described hereinabove.

The smoke detector 300 may further comprise a temperature sensor 320, a relative humidity sensor 322, and/or a voltage sensor 324 coupled to a power supply, e.g., battery (not shown). Wherein the digital processor 314 may compensate for capacitance measurements that may change under different temperature, humidity and/or voltage conditions, e.g., using look-up tables that contain calibration and compensation data for the smoke sensor ion chamber 102. In addition, the digital processor 314 may perform smoothing, time averaging, noise suppression, over sampling, and/or digital signal processing to enhance the capacitance change detection sensitivity and/or reduce noise pick-up.

Figure 4:
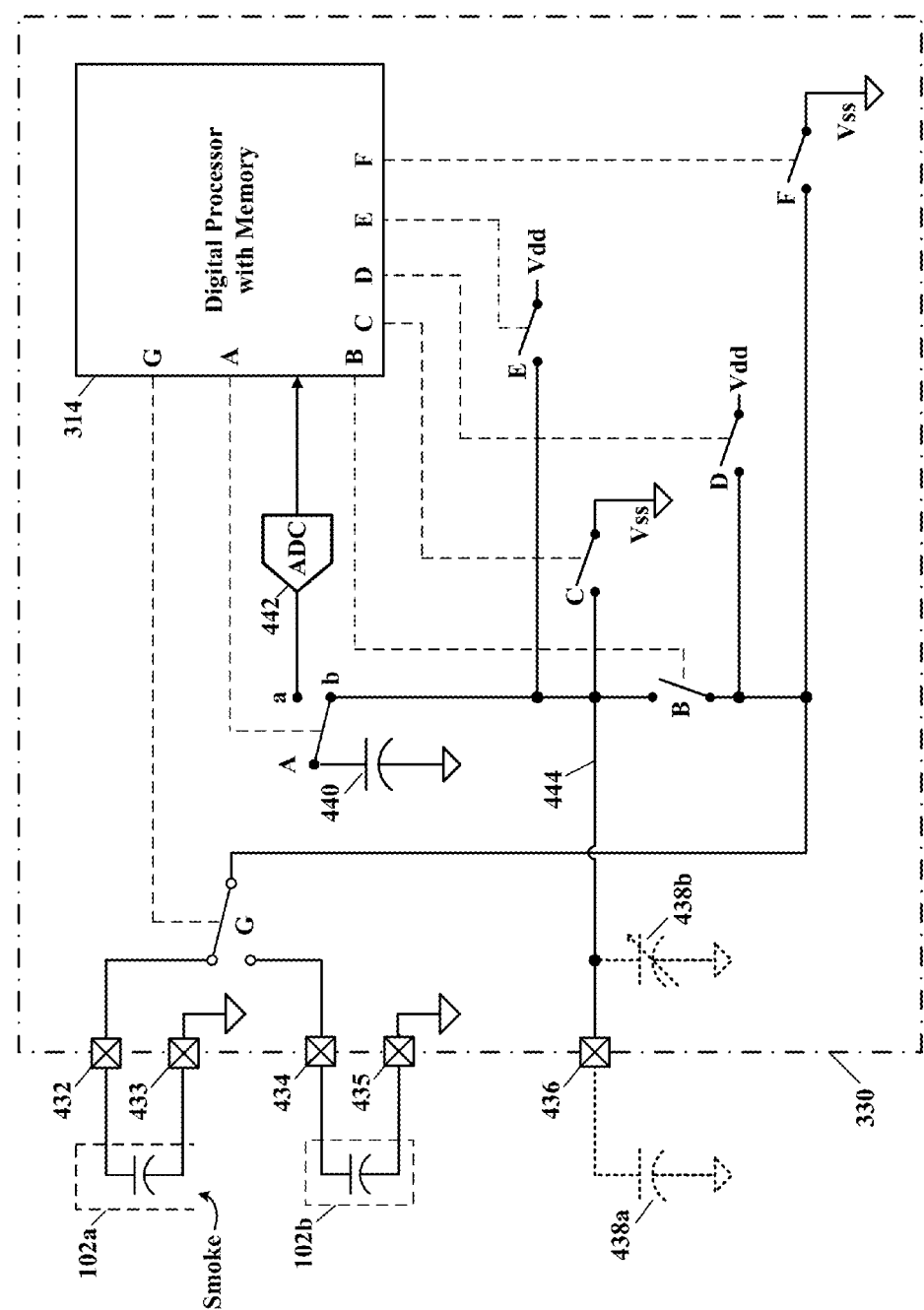
FIG. 4 illustrates a schematic block diagram of the capacitive voltage divider function shown in FIG. 3.

Referring to FIG. 4, depicted is a schematic block diagram of the capacitive voltage divider function shown in FIG. 3. The capacitive voltage divider (CVD) function uses no external components. It requires only an analog-to-digital converter (ADC) that is provided in a microcontroller, according to the teachings of this disclosure. A microcontroller 330 having ADC capabilities is applicable when using the capacitive voltage divider (CVD) method of determining the capacitance values of the ion chamber(s) 102. In the CVD method two capacitors are charged/discharged to opposite voltage values. Then the two oppositely charged capacitors are coupled together and a resulting voltage is measured on the connected two capacitors. The resulting voltage is converted to a digital representation thereof by the ADC 442 and read by the digital processor 314. This digital representation may be converted to a capacitance value by the digital processor 314 or used itself since the digital representation is proportional to the capacitance value. A sufficient change in this digital representation of the resulting voltage may be used to indicate smoke in the ion chamber 102. A further enhancement to more reliable smoke detection is to require that the sufficient change in the digital representation occurs in less than or equal to a certain time period so as to reject slow capacitance changes of the ion chamber 102 due to changes in temperature, relative humidity and/or supply voltage (e.g., battery not shown).

A multiplexer switch G may be used to selected either one of the ion chambers 102a or 102b, and may be controlled by the digital processor 314. The switches shown in FIG. 4 may be, for example but are not limited to, field effect transistor (FET) switches. The node 436 is an analog node coupled to an internal single line (conductor) analog bus 444.

The first CVD capacitor is the capacitance of the ion chamber 102, and the second CVD capacitor may be a sample and hold capacitor 444. Preferably these two capacitors have fairly close capacitive values e.g., 1:1 to about 3:1. If not, then additional capacitance may be added to either the first CVD capacitor. The reason for this in the CVD method is that part of the charge from one capacitor is transferred to the other capacitor having no charge or an opposite charge. For example, when the two CVD capacitors are equal in value, half of the charge on one will be transferred to the other capacitor. A two to one capacitance ratio will result in ⅓ of the charge being transferred to or taken from the smaller (½C) capacitor depending upon which of one the capacitors was initially charged.

When the sample and hold capacitor 440 is substantially smaller than the capacitance of the ion chamber 102, additional capacitance 438a may be added externally to node 436, and/or internal capacitance 438b may be added independently of node 436 so that the combined capacitance of the capacitors 440, 438a and/or 438b have sufficient capacitance in relation to the capacitance value of the ion camber 102 to meet the criteria above. This results in the best resolution in determining a capacitance value using the CVD method. Capacitor 440 is also the sample and hold capacitor used to sample and hold the analog voltage resulting after charge is transferred between the two CVD capacitors. Once the charge transfer is complete, an analog-to-digital converter (ADC) 442 converts the resulting charge voltage to a digital value that is read by the digital processor 314 for further processing and determination of the capacitance value or change thereof of the ion chamber 102.

In the example hereinafter presented, the capacitance values for the ion chamber 102 (first CVD capacitor), capacitor 438a (an externally connected capacitor) and/or capacitor 438b (an internally connected capacitor) may be selected in combination with the sample and hold capacitor 440 to result in a combined charge voltage of ⅓ or ⅔ of the Vdd voltage depending on whether the first CVD capacitor (ion chamber 102) is discharged to Vss or charged to Vdd, and the combination of capacitors 438 and 440 are charged to Vdd or discharged to Vss, respectively. In this example, the capacitance of the ion chamber 102 is about twice the capacitance as the capacitance of the parallel connected combination of capacitors 438 and 440. The resulting quiescent voltage after coupling the two opposite polarity charged CVD capacitors together will be about ⅓*Vdd when the ion chamber capacitance was initially discharged to Vss, and about ⅔*Vdd when the ion chamber capacitance was initially charged to Vdd.

According to various embodiments, in one measurement the housing 106 of the ion chamber 102a (FIG. 2) may be charged/discharged and then coupled in parallel with the capacitor 440 and the resulting voltage converted by the ADC 442. In another measurement the internal collector plate 104 of the ion chamber 102a may be connected in parallel with the capacitor 440. Also subtracting the ion chamber 102a resulting voltage value from the ion chamber 102b resulting voltage value and dividing by the ion chamber 102b resulting voltage value, removes temperature and battery voltage effects, leaving a resulting voltage value which is primarily affected by the presence of smoke in the ion chamber 102a.

Figure 5:
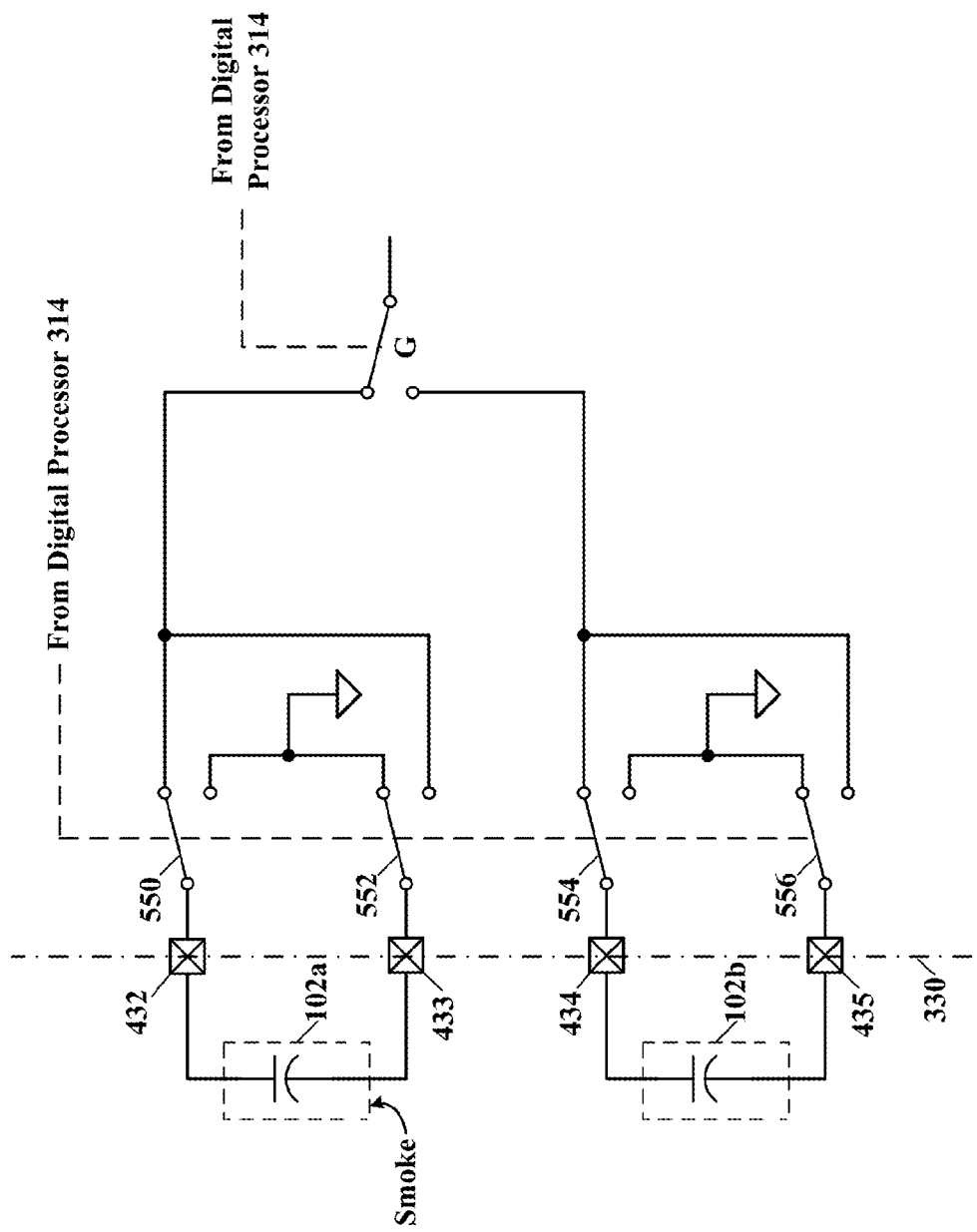
FIG. 5 illustrates a schematic block diagram of a portion of the capacitive voltage divider function shown in FIG. 3 showing switching means used in rejecting common mode leakage current, according to another specific example embodiment of this disclosure.

Referring to FIG. 5, depicted is a schematic block diagram of a portion of the capacitive voltage divider function shown in FIG. 3 showing switching means used in rejecting common mode leakage current, according to another specific example embodiment of this disclosure. Switches 550 and 552, and 554 and 556 change the polarity connections of the chambers 102a and 102b, respectively. Two CVD measurement operations for each of the chambers 102a and 102b are taken, one CVD measurement operation is taken at a first polarity and a second CVD measurement operation at a second polarity opposite the first polarity. The results of these CVD measurement operations are stored in the memory of the digital processor 314 for further computational processing, e.g., subtracting the lower CVD measurement operation capacitance value from the higher CVD measurement operation capacitance value of each chamber 102a and 102b, thereby canceling out what is caused by the leakage current 114, with a result of only a representation of the chamber ionization current 116. Since each chamber 102a and 102b is independently measured, any difference in the ionization currents 116 of the two chambers will indicate influence of smoke on the ionization of the gas in the chamber 102a. Determining a CVD operation capacitance value representing the ionization current 116 of the closed to the CVD measurement operation capacitance value representing the smoke ionization chamber 102b thereby allows a base value that can be used to track or "float" a base capacitance reference value for chamber 102a so that a small change thereof can be more easily recognized as indicating detection of smoke therein.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A method for detecting smoke, comprising the steps of:
    coupling an ionization chamber to a capacitive voltage divider (CVD) circuit;
    determining a change in a capacitance of the ionization chamber using the CVD circuit by:
    determining a first change in the capacitance of the ionization chamber when the ionization chamber is at a first polarity;
    determining a second change in the capacitance of the ionization chamber when the ionization chamber is at a second polarity;
    determining a difference between the first change and the second change; and
    using the difference in determining the change in the capacitance of the ionization chamber;
    and
    detecting the presence of smoke by detecting a predetermined change in the capacitance.

2. The method according to claim 1, where the predetermined change in the capacitance is a change in the capacitance within a certain time.

3. The method according to claim 1, where the step of determining the first or second change in the capacitance of the ionization chamber comprises the steps of:
    charging the capacitance of a first capacitor to a first voltage;
    charging the capacitance of the ionization chamber to a second voltage;
    coupling the first capacitor to the capacitance of the ionization chamber, wherein a third voltage on the first capacitor and the capacitance of the ionization chamber results;
    converting the third voltage to a digital representation thereof;
    comparing the digital representation of the converted third voltage with a previously stored digital representation thereof;
    detecting the presence of smoke when the digital representation of the converted third voltage has changed from the previously stored digital representation by at least the predetermined change; and
    storing the digital representation of the third voltage.

4. The method according to claim 1, where:
    in a first measurement, a housing of the ionization chamber is coupled to the CVD circuit; and
    in a second measurement, a collector plate of the ionization chamber is coupled to the CVD circuit.

5. The method according to claim 4, further comprising the steps of subtracting a measurement value of the first measurement from a measurement value of the second measurement then dividing by the second measurement value;
    and comparing the count numbers of subsequent time periods to determine whether the count number of any one or more of the subsequent time periods has changed by a certain number of counts.

6. The method according to claim 1, further comprising the step of compensating for temperature change with temperature information from a temperature sensor.

7. The method according to claim 1, further comprising the step of compensating for relative humidity change with relative humidity information from a relative humidity sensor.

8. The method according to claim 1, further comprising the step of compensating for voltage change with voltage information from a voltage sensor.

9. The method according to claim 3, wherein the first voltage is approximately a power supply voltage and the second voltage is approximately a power supply common.

10. The method according to claim 3, wherein the first voltage is approximately a power supply common and the second voltage is approximately a power supply voltage.

11. A method for detecting smoke using an ionization chamber, wherein the ionization chamber comprises a first ionization chamber open to smoke ingress and a second ionization chamber closed to smoke ingress, the method comprising the steps of:

coupling the ionization chamber to a capacitive voltage divider (CVD) circuit; and
determining a change in a capacitance of the ionization chamber using the CVD circuit by:
charging the capacitance of a first capacitor to a first voltage;
charging the capacitance of a first ionization chamber open to smoke entrance to a second voltage;
coupling the first capacitor to the capacitance of the first ionization chamber, wherein a third voltage on the first capacitor and the capacitance of the first ionization chamber results;
converting the third voltage to a digital representation thereof;
storing the digital representation of the third voltage;
charging the capacitance of the first capacitor to a fourth voltage;
charging the capacitance of a second ionization chamber closed to smoke entrance to a fifth voltage;
coupling the first capacitor to the capacitance of the second ionization chamber, wherein a sixth voltage on the first capacitor and the capacitance of the second ionization chamber results;
converting the sixth voltage to a digital representation thereof;
storing the digital representation of the sixth voltage;
subtracting the digital representation of the third voltage from the digital representation of the sixth voltage and dividing by the digital representation of the sixth voltage to produce a resulting representation;
comparing the resulting representation with a previously stored resulting representation;
detecting the presence of smoke when the resulting representation has changed from the previously stored resulting representation by at least the predetermined change; and
storing the resulting representation.

12. The method according to claim 11, wherein the fourth voltage is approximately a power supply voltage and the fifth voltage is approximately a power supply common.

13. The method according to claim 11, wherein the fourth voltage is approximately a power supply common and the fifth voltage is approximately a power supply voltage.

14. An apparatus for detecting smoke, comprising:
an ionization chamber coupled to a capacitive voltage divider (CVD) circuit for determining a capacitance of the ionization chamber;
wherein a predetermined change in the capacitance of the ionization chamber indicates the presence of smoke in the ionization chamber; and
circuits for alternately coupling to the ionization chamber at a first polarity for determining a first capacitance of the ionization chamber and coupling to the ionization chamber at a second polarity for determining a second capacitance of the ionization chamber, whereby a difference between the first and second capacitances is used in determining the presence of smoke in the ionization chamber.

15. The apparatus for detecting smoke according to claim 14, wherein the CVD circuit is a peripheral device in a microcontroller.

16. The apparatus for detecting smoke according to claim 15, wherein the microcontroller comprises a digital processor and memory coupled to the CVD circuit and an alarm circuit.

17. The apparatus for detecting smoke according to claim 16, further comprising a temperature sensor coupled to the digital processor and a temperature compensation look-up table stored in the memory coupled to the digital processor and used to compensate temperature induced changes of the capacitance of the ionization chamber.

18. The apparatus for detecting smoke according to claim 16, further comprising a humidity sensor coupled to the digital processor and a humidity compensation look-up table stored in the memory coupled to the digital processor and used to compensate humidity induced changes of the capacitance of the ionization chamber.

19. The apparatus for detecting smoke according to claim 16, further comprising a voltage sensor coupled to the digital processor and a voltage compensation look-up table stored in the memory coupled to the digital processor and used to compensate voltage induced changes of the capacitance of the ionization chamber.

20. The apparatus for detecting smoke according to claim 14, further comprising an audible alert actuated by the presence of smoke in the ionization chamber.

21. The apparatus for detecting smoke according to claim 14, further comprising a visual alert actuated by the presence of smoke in the ionization chamber.

22. An apparatus for detecting smoke according to claim 14, wherein the ionization chamber comprises:
a first ionization chamber open to smoke entrance; and
a second ionization chamber closed to smoke entrance;
wherein a predetermined difference in the capacitances of the first and second ionization chambers indicates the presence of smoke in the first ionization chamber.

23. The apparatus for detecting smoke according to claim 22, further comprising a smoke detection timer used in determining whether the predetermined difference occurs within a certain time period.

* * * * *